(12) United States Patent
Nakagawa (10) Patent No.: US 7,714,164 B2
(45) Date of Patent: May 11, 2010

(54) METHOD FOR PRODUCING (METH) ACRYLIC ACID

(75) Inventor: Satoshi Nakagawa, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/902,162

(22) Filed: Sep. 19, 2007

(65) Prior Publication Data

US 2008/0071111 A1    Mar. 20, 2008

(30) Foreign Application Priority Data

Sep. 20, 2006    (JP) .............................. 2006-254955

(51) Int. Cl.
*C07C 51/42*    (2006.01)
(52) U.S. Cl. .................................... 562/600
(58) Field of Classification Search ....................... None
See application file for complete search history.

(56) References Cited

U.S. PATENT DOCUMENTS

| | | | | |
|---|---|---|---|---|
| 6,677,482 | B2 * | 1/2004 | Nishimura et al. | 562/542 |
| 7,038,079 | B2 * | 5/2006 | Hirao et al. | 562/535 |
| 7,112,695 | B2 | 9/2006 | Eck et al. | |
| 7,214,816 | B2 | 5/2007 | Yada et al. | |
| 2004/0249201 | A1 | 12/2004 | Ueno et al. | |

FOREIGN PATENT DOCUMENTS

| | | |
|---|---|---|
| DE | 100 36 881 | 2/2002 |
| EP | 1 162 192 | 9/2004 |
| EP | 1 484 309 | 12/2004 |
| JP | 7-82210 | 3/1995 |

(Continued)

OTHER PUBLICATIONS

European Search Report dated Feb. 4, 2008 for EP Application No. 07 01 8315 corresponding to the present U.S. application.
Notice of Reasons for Refusal dated Aug. 5, 2008 in JP 2006-254955 which is the Japanese priority application corresponding to the present U.S. application, together with a full English translation thereof.

*Primary Examiner*—Karl J Puttlitz
(74) *Attorney, Agent, or Firm*—Wenderoth, Lind & Ponack, L.L.P.

(57) ABSTRACT

In a production method in which an acrylic acid-containing solution obtained from an acrylic acid-containing gas (or an acrylic acid-containing liquid obtained simply by subjecting the acrylic acid-containing solution to a separation process of reaction by-products) is directly subjected to a crystallization process, the crystallization process can't be carried out smoothly in an unsteady state (when the concentration of water in the acrylic acid-containing solution is high). The present invention aims to provide a method for collecting the purified acrylic acid having high purity in good yield even in an unsteady state.

When the acrylic acid-containing solutions 18 and 16 have a concentration of water higher than 10 mass % (unsteady state), the purified acrylic acid 20 and 22 or the acrylic acid-containing solution 23 containing 10 mass % or less of water is mixed therewith to make the concentration of water 10 mass % or less [a] [b]. Alternatively, when the acrylic acid-containing solutions 18 and 16 have a concentration of water higher than 10 mass %, it is used as an absorption liquid [c]. Thereafter, the crystallization process is carried out.

13 Claims, 1 Drawing Sheet

FOREIGN PATENT DOCUMENTS

| | | |
|---|---|---|
| JP | 2001-348358 | 12/2001 |
| JP | 2001-348359 | 12/2001 |
| JP | 2001-348360 | 12/2001 |
| JP | 2003-530376 | 10/2003 |
| JP | 2004-359613 | 12/2004 |
| JP | 2005-15478 | 1/2005 |
| JP | 2005-336110 | 12/2005 |

* cited by examiner

FIG.1

METHOD FOR PRODUCING (METH) ACRYLIC ACID

BACKGROUND OF THE INVENTION

1. Field of the Invention

The present invention relates to a method for producing (meth)acrylic acid, particularly to a method for producing acrylic acid in good yield without any special operation even in an unsteady state which arises at startup or due to some accident or the like.

2. Description of the Related Art

Acrylic acid and methacrylic acid (occasionally referred to as (meth) acrylic acid in this specification and claims) are useful raw materials widely used as raw materials for chemical products, and various production methods thereof are proposed. For example, as methods for producing acrylic acid industrially, a method in which propylene and/or acrolein are subjected to the catalytic gas phase oxidation is commonly used, and a method in which an acrylic acid-containing gas obtained by the catalytic gas phase oxidation method is condensed or absorbed in an absorption liquid to make an acrylic acid-containing solution followed by being subjected to distillation and crystallization to obtain a purified acrylic acid is proposed.

As a purification process, in addition to the method described above, for example, in Japanese Patent Publication No. 2005-15478A, a method in which an acrylic acid-containing gas is brought in contact with an aqueous solution for absorption in an absorption column to obtain an acrylic acid-containing solution, and the acrylic acid-containing solution as a crude acrylic acid is directly subjected to a crystallization process, and a distillate obtained by distilling a residual mother liquid discharged in the crystallization process is circulated in the absorption column is proposed. Such circulation to introduce a high-concentration acrylic acid-containing solution in the crystallization process has an effect of obtaining a highly purified acrylic acid with good absorption efficiency, and even more, the production process is easy and simple.

In Japanese Patent Publication No. 2003-530376A, the purification of acrylic acid using a cleaning column having a function of forcible transport of crystal for the crystallization of acrylic acid is proposed.

SUMMARY OF THE INVENTION

In accordance with the methods described in Japanese Patent Publication No. 2005-15478A and Japanese Patent Publication No. 2003-530376A, it is possible to obtain acrylic acid having high purity by easy and simple processes, but both of the above methods are only effective when the purification process of acrylic acid is already put in a steady state, and when it is in an unsteady state, for example, when the concentration of water in the acrylic acid-containing solution becomes higher at startup or due to some accident, the crystallization process is not smoothly carried out and it will be difficult to obtain a purified acrylic acid having high purity and the yield will be lower; in a worse case, it will be difficult to continue the operation itself.

Therefore, when the concentration of water in the acrylic acid-containing solution is high, the acrylic acid-containing solution has to be disposed of without being subjected to crystallization process, or has to be subjected newly to the water separation operation to lower the concentration of water before being supplied to a device for the crystallization process. As a result, the yield of acrylic acid is lowered in the entire process, and the cost increases due to the additional water separation operation.

The problem described above does not occur in a method in which the crystallization is performed after an acrylic acid-containing solution is distilled, and as described above, it is a new problem found in a production method in which an acrylic acid-containing solution obtained by condensing an acrylic acid-containing gas or bringing it in contact with an absorption liquid is directly subjected to a crystallization process. There is also a case in which the acrylic acid-containing liquid obtained from the acrylic acid-containing gas is subjected to a separation process step followed by a crystallization process to separate reaction by-products, but regardless of whether or not the separation process step is carried out, the crystallization process can't be carried out smoothly when the acrylic acid-containing solution to be subjected to the crystallization process has a high concentration of water.

The present invention has been accomplished in view of the above circumstances. The object of the present invention is, even when the (meth) acrylic acid-containing solution which is a raw liquid material in a crystallization process has a high concentration of water, to enable the collection of the purified (meth) acrylic acid having high purity and to increase the yield of (meth)acrylic acid throughout the entire process, without increasing the cost too much.

The present inventor intensively examined the above problems, and accomplished the present invention with discoveries that (1) when the acrylic acid-containing solution to be subjected to the crystallization process contains more than 10 mass % of water, purity and yield of the resultant purified acrylic acid are lowered; (2) by mixing an acrylic acid-containing solution having sufficiently low concentration of water or a purified acrylic acid in the acrylic acid-containing solution containing more than 10 mass % of water, the concentration of water thereof can be made 10 mass % or less, and if subjecting the resultant solution to the crystallization process, the purified acrylic acid having high purity can be obtained in good yield; or (3) if the acrylic acid-containing solution contains more than 10 mass % of water, it is to be used as an absorption liquid in an absorption process step, and to be circulated like this so that an acrylic acid-containing solution containing 10 mass % or less of water can be obtained, and if subjecting the resultant solution to the crystallization process, the purified acrylic acid having high purity can be obtained in good yield; in addition, with respect to methacrylic acid, the purified methacrylic acid having high purity can also be obtained in good yield in a same manner as acrylic acid.

Namely, the method for producing (meth)acrylic acid according to the present invention comprises obtaining a (meth)acrylic acid-containing gas from a raw material of (meth) acrylic acid by a catalytic gas phase oxidation reaction and obtaining a (meth) acrylic acid-containing solution from the (meth)acrylic acid-containing gas followed by subjecting the (meth)acrylic acid-containing solution to a crystallization process or subjecting the (meth)acrylic acid-containing solution obtained after separating the reaction by-products therefrom to a crystallization process, thereby producing the purified (meth) acrylic acid; in the method, it is characterized that the (meth)acrylic acid-containing solution or the (meth) acrylic acid-containing solution upstream thereof (for example, a (meth)acrylic acid-containing solution prior to a separation process in a production method including a step of separation process of reaction by-products) is mixed with a purified (meth)acrylic acid and/or a (meth)acrylic acid-containing solution containing 10 mass % or less of water to make the concentration of water 10 mass % or less followed by carrying out a crystallization process when the concentration of water in the (meth)acrylic acid-containing solution to be subjected to the crystallization process is higher than 10 mass %. A method for obtaining a (meth) acrylic acid-containing solution from a (meth) acrylic acid-containing gas includes a method condensing the (meth)acrylic acid-containing gas and a method obtaining the (meth) acrylic acid-containing solution by bringing the (meth)acrylic acid-containing gas in contact with an absorption liquid. The absorption liquid includes water and high boiling point solvents.

As the purified (meth)acrylic acid to be mixed in the (meth) acrylic acid-containing solution having a concentration of water higher than 10 mass %, a purified (meth)acrylic acid which has been obtained separately may be used (for example, a purified (meth) acrylic acid produced during an operation in a steady state in the production line may be stored for use later, or a purified (meth) acrylic acid obtained in another production line (in addition to the one obtained by a crystallization process, it may be the one obtained by a distillation process) may be used), or a purified (meth) acrylic acid obtained in the crystallization process may be circulated for use while the production process is in operation.

When the purified (meth) acrylic acid to be mixed is the one obtained by the same production method (namely, the purified (meth)acrylic acid obtained by subjecting a (meth)acrylic acid-containing solution produced from a (meth)acrylic acid-containing gas obtained by the catalytic gas phase oxidation reaction to a crystallization process or subjecting the (meth) acrylic acid-containing solution obtained after separating the reaction by-products therefrom to a crystallization process), it is preferable because impurities included in a slight amount therein do not affect the production method.

Additionally, there are advantages when the follows are used as the purified (meth)acrylic acid. Namely, [1]: initially purified (meth)acrylic acid obtained at the onset of the operation is discharged while cleaning each part such as a pipe and a tank, so that it contains various dirt. Therefore, although the initially purified (meth) acrylic acid has to be disposed of under ordinary circumstances, it can be repurified by bringing it back to the previous step for use just as the present invention, and accordingly, the ratio of loss in the whole process can be reduced. [2]: when the production line is brought to an emergency stop and the like for some reason, the purified (meth)acrylic acid is not transported to a predetermined tank (namely, it is not subjected to a polymerization-prevention treatment), but stored in the production line. When the accumulation time (stopping time) becomes long, a polymer and the like may be formed to lower the purity of the purified (meth) acrylic acid. However, by bringing it back to the previous step for use without disposing of it just as the present invention, the ratio of loss in the whole process can be reduced.

Additional, as the (meth)acrylic acid-containing solution containing 10 mass % or less of water to be mixed in the (meth)acrylic acid-containing solution containing more than 10 mass % of water, the (meth)acrylic acid-containing solution containing 10 mass % or less of water obtained in a process producing (meth)acrylic acid may be stored for use.

In addition, the method for producing (meth) acrylic acid according to the present invention comprises obtaining a (meth)acrylic acid-containing gas from a raw material of (meth)acrylic acid by the catalytic gas phase oxidation reaction and obtaining a (meth)acrylic acid-containing solution from the (meth)acrylic acid-containing gas followed by subjecting the (meth)acrylic acid-containing solution to a crystallization process or subjecting the (meth)acrylic acid-containing solution obtained after separating the reaction by-products therefrom to a crystallization process, thereby producing the purified (meth)acrylic acid; in the method, it is characterized that the (meth)acrylic acid-containing solution or the (meth) acrylic acid-containing solution upstream thereof is used as an absorption liquid when the (meth) acrylic acid-containing solution to be subjected to the crystallization process contains more than 10 mass % of water.

In this case, as an absorption liquid used for absorption, the (meth)acrylic acid-containing solution containing more than 10 mass % of water may be used; alternatively, the (meth) acrylic acid-containing solution containing more than 10 mass % of water may be concomitantly used with a usual absorption liquid. In addition to a use for absorption by being circulated during an operation of the production process, the (meth) acrylic acid-containing solution containing more than 10 mass % of water can be used as an absorption liquid after temporarily being stored. Further, in a case wherein it is used as an absorption liquid after being temporarily stored as described above, it may be used as an absorption liquid after the (meth) acrylic acid-containing solution containing 10 mass % or less of water can be obtained in a stable manner, (in this case, it is preferred to use a necessary amount of the liquid little by little to an extent that the (meth)acrylic acid-containing solution obtained in the production process can maintain the concentration of water of 10 mass % or less), or it may be used as an absorption liquid in a state where only a (meth) acrylic acid-containing solution containing more than 10 mass % of water can be obtained.

As the method for supplying the (meth)acrylic acid-containing solution containing more than 10 mass % of water to the absorption column, a supply line of a (meth) acrylic acid-containing solution containing more than 10 mass % of water may be connected to a supply line of a usual absorption liquid so as to supply the solution to the absorption column; alternatively, a supply line of the (meth)acrylic acid-containing solution containing more than 10 mass % of water alone may be disposed in the absorption column (in a manner that the supply line has an opening at a position higher than a gas feed inlet of the absorption column) so as to supply the solution directly to the absorption column.

In addition, the method for producing (meth) acrylic acid according to the present invention comprises obtaining a (meth)acrylic acid-containing gas from a raw material of (meth)acrylic acid by the catalytic gas phase oxidation reaction, and obtaining a (meth)acrylic acid-containing solution from the (meth) acrylic acid-containing gas, followed by subjecting the (meth)acrylic acid-containing solution to a crystallization process or subjecting the (meth)acrylic acid-containing solution obtained after separating the reaction by-products therefrom to a crystallization process, thereby producing the purified (meth)acrylic acid; in the method, it is characterized that when the (meth)acrylic acid-containing solution contains more than 10 mass % of water, it is temporarily stored, and when the (meth)acrylic acid-containing solution containing 10 mass % or less of water can be obtained in a stable manner, the stored (meth)acrylic acid-containing solution containing more than 10 mass % of water is mixed therein to an extent that the concentration of water is maintained at 10 mass % or less, followed by being subjected to the crystallization process.

Namely, in a case where the (meth)acrylic acid-containing solution contains more than 10 mass % of water, it is temporarily stored, and when the purification process comes to a steady state, the (meth) acrylic acid-containing solution containing more than 10 mass % of water which has been stored is mixed in a (meth) acrylic acid-containing solution containing 10 mass % or less of water. However, mixing is made to an extent that the concentration of water is retained 10 mass % or less, and the resultant (meth)acrylic acid-containing solution containing 10 mass % or less of water is to be supplied to the step of the crystallization process.

With respect to the production methods, methods for obtaining a (meth)acrylic acid-containing solution from a (meth) acrylic acid-containing gas include a method condensing a(meth)acrylic acid-containing gas and a method obtaining a (meth)acrylic acid-containing solution by bringing the (meth)acrylic acid-containing gas in contact with an absorption liquid and the like.

Further, in the present invention, each of the above methods may be used in combination.

In the method for producing (meth) acrylic acid, when the method obtaining a (meth)acrylic acid-containing solution by bringing a (meth) acrylic acid-containing gas in contact with an absorption liquid is employed in which water is used as the absorption liquid, the concentration of water tends to be high so that it is particularly useful to apply the present invention thereto.

The reaction by-products include acrolein, methacrolein (hereinafter occasionally referred to as (meth) acrolein) and the like. Additionally, a case in which the (meth)acrylic acid-containing solution to be subjected to the crystallization process contains 10 mass % or less of water (when it contains 10 mass % or less of water even without carrying out a measure according to the present invention) is called a steady state, while a case wherein the (meth) acrylic acid-containing solution to be subjected to the crystallization process contains more than 10 mass % of water(when it contains more than 10 mass % of water without carrying out a measure according to the present invention) is called an unsteady state.

DESCRIPTION OF THE PREFERRED EMBODIMENT

Figure 1:
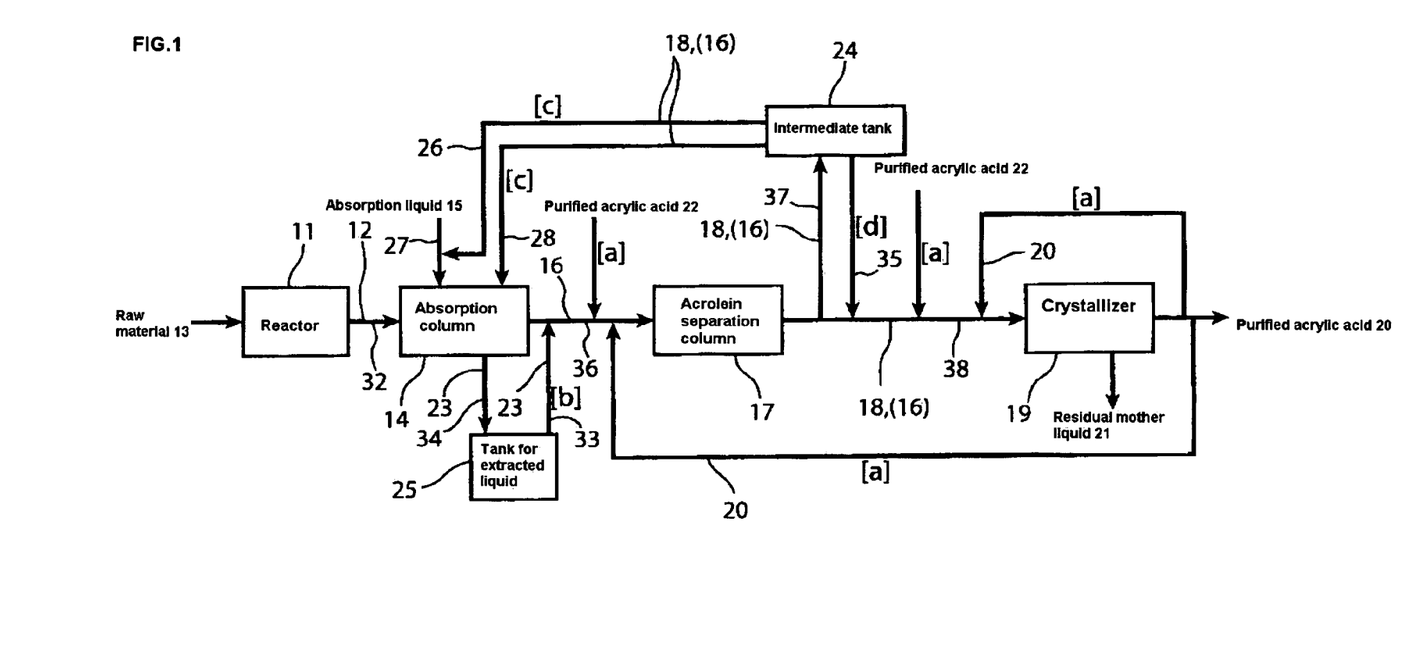
FIG. 1 is a block diagram showing an example of a method for producing acrylic acid according to the present invention.

FIG. 1 is a block diagram showing an example of the method for producing acrylic acid. First, a method for producing acrylic acid (purification process) in a steady state will be explained with reference to FIG. 1.

In a reactor 11, an acrylic acid-containing gas 12 is generated from a raw material of acrylic acid 13 by the catalytic gas phase oxidation reaction, and the acrylic acid-containing gas 12 is introduced to an absorption column 14 (line 32). In the absorption column 14, an absorption liquid 15 and the acrylic acid-containing gas 12 are brought in contact to obtain an acrylic acid-containing solution 16 (absorption step). The methods of the contact include cross-flow contact, counter-flow contact and the like. In the present embodiment, an absorption method wherein the absorption liquid is supplied from outside the system as a method for obtaining the acrylic acid-containing solution 16 will be described; however, for example, in a condensing method, the absorption liquid is not to be added from outside the system.

Next, the acrylic acid-containing solution 16 is introduced to an acrolein separation column 17 (line 36), and acrolein is subjected to a separation process (acrolein separation process step). Methods for the separation process include distillation, diffusion or the like, and may be suitably selected depending on the concentrations of acrylic acid and acrolein contained.

The step of the acrolein separation process can be skipped when the acrylic acid-containing solution 16 does not contain acrolein. Furthermore, if the acrylic acid-containing solution 16 is subjected to a crystallization process (crystallizer 19) via a step of the acrolein separation process, lowering of the concentration of water can be expected in the step of the acrolein separation process. In this view, in a method wherein the acrylic acid-containing solution 16 obtained by condensing the acrylic acid-containing gas 12 or bringing it in contact with an absorption liquid is directly (i.e., without going through a step of the acrolein separation process) subjected to a crystallization process, it is preferred to obtain an acrylic acid-containing liquid having a high concentration of acrylic acid in an absorption step compared with that going through a step of the acrolein separation process.

An acrylic acid-containing solution 18 obtained by the separation process or the acrylic acid-containing solution 16 is supplied to the crystallizer 19 (line 38) to obtain the purified acrylic acid 20. The crystallization method at this time is not limited, and either a continuous type or a batch-type crystallizer may be used, and the crystallizer is not limited to one-stage, but may be two or more stages for use in implementing the method. For example, as a continuous type crystallizer, a column-shaped one having a crystallization part, a solid-liquid separation part and a crystal purification part all united in one can be used. In the figure, reference numeral 21 denotes a residual mother liquid discharged from the crystallizer 19. In Japanese Patent Publication No. 2005-15478A, at least a part of the residual mother liquid 21 is distilled, and the resultant distillate is to be supplied to the absorption column 14.

Next, a method for producing acrylic acid (purification process) in an unsteady state will be explained.

When the acrylic acid-containing solution 18 (the acrylic acid-containing solution 16 when the acrolein separation process is not carried out) contains more than 10 mass % of water, any one of following [a] to [d] or a combination of two or more thereof and the like (hereinafter occasionally referred to as measures [a] to [d]) are employed so that the concentration of water in the acrylic acid-containing solution to be supplied to the crystallizer 19 is made 10 mass % or less.

[a]: The purified acrylic acid 20 discharged from the crystallizer 19, or the purified acrylic acid 22 obtained in another production process is mixed in the acrylic acid-containing solution 18 (the acrylic acid-containing solution 16 when the acrolein separation process is not carried out) of the line 38, and the mixture is supplied to the crystallizer 19. Alternatively, the purified acrylic acid 20 or 22 is mixed in the acrylic acid-containing solution 16 of the line 36 followed by subjecting the mixture to the acrolein separation process, and the resultant acrylic acid-containing solution 18 is supplied to the crystallizer 19.

[b]: An acrylic acid-containing solution having a low concentration of water obtained from the absorption column 14 in a steady state (hereinafter referred to as extracted liquid) is stored in a tank 25 used for the extracted liquid (line 34) in advance, and when the acrylic acid-containing solution 16 containing more than 10 mass % of water is discharged from the absorption column 14, the extracted liquid 23 is mixed in the acrylic acid-containing solution 16 (line 33). If necessary, the mixture is subjected to the acrolein separation process followed by being supplied to the crystallizer 19.

[c]: The acrylic acid-containing solution 18 or 16 having a high concentration of water is supplied from an absorption liquid feed inlet of the absorption column 14 (namely, the acrylic acid-containing solution 18 or 16 having a high concentration of water is supplied to the absorption column 14 from an intermediate tank discharge line 26 via an absorption liquid supply line 27) or from a feed inlet for the return of the acrylic acid-containing solution (the feed inlet for the return of the acrylic acid-containing solution is disposed at a position higher than the gas feed inlet) connected with the absorption column 14 (namely, the acrylic acid-containing solution 18 or 16 having a high concentration of water is supplied to the absorption column 14 from the intermediate tank discharge line 28). In this manner, the acrylic acid-containing solutions 18 and 16 having a high concentration of water are circulated as absorption liquids, thereby the acrylic acid component is condensed so that the acrylic acid-containing solution 16 having a low concentration of water can be obtained. If the amount of the acrylic acid-containing solution 18 or 16 having a high concentration of water is more than that needed in an absorption liquid in the absorption column 14, it is preferable that the acrylic acid-containing solution 18 or 16 is stored temporarily in an intermediate tank 24, and an amount needed for absorption in the absorption column 14 is supplied little by little. When the amount of the acrylic acid-containing solution 18 or 16 having a high concentration of water is sufficiently smaller than that needed in the absorption liquid in the absorption column 14, the acrylic acid-containing solution 18 or 16 may be supplied to the absorption liquid feed inlet without going through the intermediate tank 24. Further, as a timing for supplying an acrylic acid-containing solution having a high concentration of water in the intermediate tank 24 to the absorption column 14, it may be when the concentration of water in the acrylic acid-containing solution 16 discharged from the absorption column 14 becomes 10 mass % or less, or before the concentration of water becomes 10 mass % or less (when it is higher than 10 mass %).

[d]: When the acrylic acid-containing solution 18 or 16 having a high concentration of water is temporarily stored in the intermediate tank 24 (line 37) and the purification process of acrylic acid comes to a steady state, the solution is brought back from the intermediate tank 24 through the line 35 to the original line (line 38), thereafter is mixed with the acrylic acid-containing solution 18 or 16 in a steady state, and the resultant mixture is supplied to the crystallizer 19. However, in order that the concentration of water in the acrylic acid-containing solution after being mixed does not become higher than 10 mass %, the amount of the acrylic acid-containing solution supplied from the intermediate tank 24 is to be adjusted.

In accordance with [a] to [d] described above, by making the acrylic acid-containing solution to be supplied to the crystallizer 19 contain 10 mass % or less of water, a step for crystallization can be carried out smoothly without any special operation, and the purified acrylic acid with high purity can be produced in good yield.

As a timing for switching from an operation mode implementing the measures [a] to [d] (a method using any one of [a] to [d], or a combination of two or more thereof) (an operation mode in which measures for an unsteady state are implemented) to an operation mode for a steady state (steady operation), the operation can be switched to the steady operation not only immediately after the concentration of water in the acrylic acid-containing solution 18 (the acrylic acid-containing solution 16 in a case where an acrolein separation process is not carried out) becomes 10 mass % or less, but also at a stage where the concentration of water in the acrylic acid-containing solution 18 (or the acrylic acid-containing solution 16) becomes 8 mass % or less, and further, 5 mass % or less.

Even though the acrylic acid-containing solution 18 (16) contains 10 mass % or less of water, it cannot be said that the process is in a sufficiently stable condition as soon as the concentration of water becomes 10 mass % or less, so that there will possibly be a need to switch to the operation mode implementing the measures [a] to [d] again in a short time. Accordingly, in view of complication in switching, it is preferred to switch to the steady operation after the concentration of water becomes 8 mass % or less, or, further, 5 mass % or less, which is a more stable condition. Additionally, by implementing the measures [a] to [d], it becomes possible to introduce an acrylic acid-containing solution having a lower concentration of water to the crystallizer, so the crystallization process of the solution having a lower concentration of water can be carried out more smoothly, and product specifications will also become higher. Therefore, from a viewpoint of the concentration of water, it is preferable to switch to the steady operation after the concentration of water in the acrylic acid-containing solution 18(16) becomes 8 mass % or less, or, further, 5 mass % or less.

On the other hand, in order to lower the concentration of water, it takes longer to implement the above measures [a] to [d] (compared with a case wherein the concentration of water becomes 10 to 8 mass %, it takes longer for the concentration of water to become 8 to 5 mass %, and it takes further longer for the concentration of water to become 5 mass % or less); therefore, an operation mode implementing the measures [a] to [d] (unsteady operation) needs to be continued for a long period of time. Therefore, from this viewpoint, it is preferred to switch to the steady operation at a stage in which the concentration of water in the acrylic acid-containing solution 18 (16) is not lowered so much (for example, a concentration of water of 8 to 5 mass %, preferably 10 to 8 mass %)

Here, an absorption method for obtaining an acrylic acid-containing solution from an acrylic acid-containing gas using the absorption liquid described above will be described.

As an aqueous solution for absorption, a wide range of aqueous solutions may be used as long as they can absorb acrylic acid, and a condensate obtained by cooling and condensing a gas discharged from the top of the absorption column (which is discharged in order to minimize the loss of acrylic acid discharged outside the system) is preferably used as an aqueous solution for absorption. The condensate often contains acrylic acid, so if it is used as the absorption aqueous solution, the acrylic acid-containing solution having a high concentration of acrylic acid can be obtained. It is also a preferred embodiment that the gas discharged from the top of the absorption column is partially or fully recycled in the reactor.

The aqueous solution for absorption is preferably introduced to the absorption column at a temperature of 0 to 50° C., more preferably 10 to 40° C.

A ratio of mass flow rate of an aqueous solution for absorption to be newly supplied from outside to an acrylic acid-containing gas may be suitably selected in accordance with an objective acrylic acid concentration, and preferably 0.1 to 1.5 times the mass flow rate of acrylic acid included in the acrylic acid-containing gas, more preferably 0.1 to 1.0 times, even more preferably 0.15 to 0.8 times. Then an aqueous solution for absorption having this mass flow rate is subjected to counter-flow contact with an acrylic acid-containing gas to absorb acrylic acid. If the ratio of mass flow rate is lower than 0.1 times, efficiency of the acrylic acid absorption column may be extremely lowered.

In addition, since acrylic acid is a polymerizable material, for a purpose to prevent the polymerization, one or more compounds selected from the group consisting of a N-oxyl compound, a phenol compound, a manganese salt such as manganese acetate and the like, a dialkyldithiocarbamate copper salt such as dibutylcarbamate copper and the like, a nitro compound, an amine compound and phenothiazine may be included in the aqueous solution for absorption (refer to Japanese Patent Publication No. 2001-348360A, Japanese Patent Publication No. 2001-348358A, Japanese Patent Publication No. 2001-348359A and the like).

The acrylic acid absorption column is generally operated under a normal pressure or above. During the steady operation, the column-top pressure (gauge pressure) is preferably at 0 to 0.4 MPa, more preferably at 0 to 0.1 MPa, even more preferably at 0 to 0.03 MPa. If it is lower than 0 MPa (gauge pressure), a decompressor becomes necessary and it costs equipment and utilities expenses, while if it is higher than 0.4 MPa (gauge pressure),the temperature of the absorption column needs to be increased considerably in order to discharge low boiling point substances, so that the absorption efficiency may be lowered.

A column top temperature of an absorption column is generally from 30 to 85° C., preferably from 40 to 80° C.

Under the absorption condition described above, in the present embodiment, an acrylic acid-containing solution with a following blending ratio can be obtained: acrylic acid:80 to 98 mass %, water:1 to 19 mass %, other impurities (acids such as acetic acid, maleic acid, propionic acid and the like, aldehydes such as furfural, formaldehyde and the like):1 to 10 mass %.

With respect to the method for producing methacrylic acid (purification process), the crystallization step can also be carried out smoothly without any special operation in a same manner as the acrylic acid, thereby a purified methacrylic acid with high purity can be produced in good yield.

The concentration of water in the acrylic acid-containing solution (or the methacrylic acid-containing solution) can be determined by Karl Fischer's method. The acrylic acid concentration in the acrylic acid-containing solution (the methacrylic acid concentration in the methacrylic acid-containing solution) can be determined by any one of gas chromatography analysis, electrical conductivity measurement and neutralization titration.

Hereinafter, the present invention will be described in more detail with reference to examples, but the present invention is not restricted by the following examples and can be suitably modified within the scope described above or below and such modifications are also included in the technical scope of the present invention.

EXAMPLE 1

The acrylic acid-containing gas 12 obtained by the catalytic gas phase oxidation method was introduced to the absorption column 14 to be brought in counter-flow contact with the absorption liquid 15, thereby the acrylic acid-containing solution 16 was obtained. The liquid composition of the acrylic acid-containing solution 16 comprised 65.0 mass % of acrylic acid, 20.0 mass % of water, and 15.0 mass % of other impurities.

The purified acrylic acid 20 (the composition of the purified acrylic acid comprised 99.4 mass % of acrylic acid, 0.004 mass % of water and 0.6 mass % of other impurities) obtained in advance during an operation in a steady state was mixed in the acrylic acid-containing solution 16 to give a mixture thereof. The mixing mass ratio of the acrylic acid-containing solution to the purified acrylic acid was 2:5. The above mixture contained 5.7 mass % of water, 89.6 mass % of acrylic acid, and 4.7 mass % of other impurities.

The above mixture was supplied to the crystallizer 19 to be subjected to crystallization. The resultant acrylic acid had a purity of 99.4 mass %. The purification yield of acrylic acid was 99.9%.

In this Example 1, although no special operation other than mixing the purified acrylic acid was carried out, purified acrylic acid having high purity could be produced in good yield as described above.

EXAMPLE 2

The acrylic acid-containing gas 12 obtained by the catalytic gas phase oxidation method was brought in counter-flow contact with the absorption liquid 15 in the absorption column 14 to obtain the acrylic acid-containing solution 16. The liquid composition of the acrylic acid-containing solution 16 comprised 75.0 mass % of acrylic acid, 20.0 mass % of water, and 5.0 mass % of other impurities.

On the other hand, during an operation in a steady state, an acrylic acid-containing solution containing 10 mass % or less of water discharged from the absorption column 14 was extracted and stored in advance (the acrylic acid-containing solution is referred to as extracted liquid) (tank 25 for the extracted liquid), and the extracted liquid 23 was mixed with the acrylic acid-containing solution 16 of the line 36 (a mixture). The mixing mass ratio of the acrylic acid-containing solution to the extracted liquid was 1:20. The composition of the extracted liquid 23 comprised 88.7 mass % of acrylic acid, 4.4 mass % of water, and 6.9 mass % of other impurities. The liquid composition of the above mixture comprised 88.0 mass % of acrylic acid, 5.1 mass % of water, and 6.8 mass % of other impurities.

The mixture was supplied to the crystallizer 19 to be subjected to crystallization. The resultant acrylic acid had a purity of 99.4 mass %. The purification yield of acrylic acid was 99.9%.

In this Example 2, too, although no special operation other than mixing the acrylic acid-containing solution having a low concentration of water was carried out, the purified acrylic acid having high purity could be produced in good yield as described above.

EXAMPLE 3

The acrylic acid-containing gas 12 obtained by the catalytic gas phase oxidation method was subjected to counter-flow contact with the absorption liquid 15 in the absorption column 14 to obtain the acrylic acid-containing solution 16. The liquid composition of the acrylic acid-containing solution 16 comprised 75.0 mass % of acrylic acid, 15.0 mass % of water and 10.0 mass % of other impurities.

The acrylic acid-containing solution 16 was stored in the intermediate tank 24 (the stored acrylic acid-containing solution is occasionally referred to as a stored acrylic acid-containing solution), and from the tank, the acrylic acid-containing solution was supplied from an absorption liquid feed inlet of the absorption column 14 in a manner that it was included in an amount of 20 mass % relative to the amount of the absorption liquid (line 27 via line 26). Then, this operation was continued until the concentration of water in the acrylic acid-containing solution 16 (line 36) discharged from the absorption column 14 became 10 mass % or less.

After that, it was confirmed that the acrylic acid-containing solution 16 discharged from the absorption column 14 had a sufficiently low concentration of water which can be obtained in a stable manner (specifically, the liquid composition comprised 86.0 mass % of acrylic acid, 8.0 mass % of water, and 6.0 mass % of other impurities), and the acrylic acid-containing solution 16 having a low concentration of water was supplied to the crystallizer 19 for crystallization.

The resultant acrylic acid showed a purity of 99.4 mass %, and the purification yield of acrylic acid was 99.9%.

In this Example 3, although no special operation was carried out except that the acrylic acid-containing solution containing more than 10.0 mass % of water was brought back to the absorption column as the absorption liquid, the purified acrylic acid having high purity could be produced in good yield as described above.

EXAMPLE 4

The acrylic acid-containing gas 12 obtained by the catalytic gas phase oxidation method was subjected to counter-low contact with the absorption liquid 15 in the absorption column 14 to obtain the acrylic acid-containing solution 16. Next, the acrylic acid-containing solution 16 was supplied to the acrolein separation column 17 for subjecting acrolein and the like to separation by distillation, thereby the acrylic acid-containing solution 18 with acrolein and the like removed was obtained. The liquid composition of the acrylic acid-containing solution 18 comprised 67.0 mass % of acrylic acid, 20.0 mass % of water and 13.0 mass % of other impurities.

The purified acrylic acid 20 (the composition of the purified acrylic acid comprised 99.4 mass % of acrylic acid, 0.004 mass % of water, and 0.6 mass % of other impurities) obtained in advance during an operation in a steady state was mixed in the acrylic acid-containing solution 18 (line 38) to be supplied to the crystallizer 19. The mixing mass ratio of the acrylic acid-containing solution to the purified acrylic acid was 2:5. The mixture contained 5.7 mass % of water, 90.1 mass % of acrylic acid, and 4.1 mass % of other impurities.

The acrylic acid obtained by crystallizing the mixture had a purity of 99.4 mass %. The purification yield of acrylic acid was 99.9%.

In the Example 4, too, although no special operation other than mixing the purified acrylic acid was carried out, the purified acrylic acid having high purity could be produced in good yield as described above.

EXAMPLE 5

The acrylic acid-containing gas 12 obtained by the catalytic gas phase oxidation method was subjected to counter-flow contact with the absorption liquid 15 in the absorption column 14 to obtain the acrylic acid-containing solution 16. The liquid composition of the acrylic acid-containing solution 16 comprised 65.0 mass % of acrylic acid, 20.0 mass % of water, and 15.0 mass % of other impurities.

The acrylic acid-containing solution 16 was supplied to the crystallizer 19. In the crystallization process, the above Examples 1 to 4 showed an acrylic acid crystallization speed equivalent to that at a time of a steady operation, compared with this, the crystallization speed of acrylic acid in Example 5 is slow so that the crystal amount obtained in an equivalent time to that in Examples 1 to 4 was very small. The crystallization speed became slow probably because the melting point of the acrylic acid-containing solution was lowered due to the high concentration of water in the acrylic acid-containing solution 16 so that the heat exchange efficiency with the refrigerant became poor. Further, a change in the solution component accompanied with the progress of crystallization led to further lowering of the melting point so that it became difficult to continue the crystallization step and thus the operation was stopped.

EXAMPLE 6

The acrylic acid-containing gas 12 obtained by the catalytic gas phase oxidation method was subjected to counter-flow contact with the absorption liquid 15 in the absorption column 14, thereby the acrylic acid-containing solution 16 was obtained. The liquid composition of the acrylic acid-containing solution 16 comprised 65.0 mass % of acrylic acid, 20.0 mass % of water, and 15.0 mass % of other impurities.

On the other hand, the purified acrylic acid 20 (the composition of the purified acrylic acid comprised 99.4 mass % of acrylic acid, 0.004 mass % of water and 0.6 mass % of other impurities) obtained in advance during an operation in a steady state was mixed in the acrylic acid-containing solution 16 in a manner that the mass ratio of the acrylic acid-containing solution to the purified acrylic acid became 2:1, and the resultant mixture was supplied to the crystallizer 19. The mixture contained 13.3 mass % of water, 76.5 mass % of acrylic acid, and 10.2 mass % of other impurities.

In the above crystallizer 19, only 60 mass % of the acrylic acid included in the mixture could be crystallized. It is probably because the melting point of the acrylic acid-containing solution was lowered since the concentration of water in the acrylic acid-containing solution supplied to the crystallizer 19 was high, resulting in the lower crystallization rate. Therefore, it became difficult to continue the crystallization process, and thus the operation was stopped.

EXAMPLE 7

The acrylic acid-containing gas 12 obtained by the catalytic gas phase oxidation method was subjected to counter-flow contact with the absorption liquid 15 in the absorption column 14 to obtain the acrylic acid-containing solution 16. The liquid composition of the acrylic acid-containing solution 16 comprised 65.0 mass % of acrylic acid, 20.0 mass % of water, and 15.0 mass % of impurities.

The purified acrylic acid 20 (the composition of the purified acrylic acid comprised 99.4 mass % of acrylic acid, 0.004 mass % of water, and 0.6 mass % of other impurities) obtained in advance during an operation in a steady state was mixed in the acrylic acid-containing solution 16 in a manner that the ratio of the acrylic acid-containing solution to the purified acrylic acid became 1:1, thereafter supplied to the crystallizer 19. The mixture contained 10.0 mass % of water, 82.2 mass % of acrylic acid, and 7.8 mass % of other impurities.

The resultant acrylic acid showed a purity of 99.4 mass %. The purification yield of acrylic acid was 96.0%.

In this Example 7, although no special operation other than mixing the purified acrylic acid was carried out, the purified acrylic acid having high purity could be produced as described above.

EXAMPLE 8

The acrylic acid-containing gas 12 obtained by the catalytic gas phase oxidation method was subjected to counter-flow contact with the absorption liquid 15 in the absorption column 14 to obtain the acrylic acid-containing solution 16. Since the acrylic acid-containing solution 16 had a high concentration of water up to 20.0 mass %, the acrylic acid-containing solution 16 was stored in the intermediate tank 24

(the stored acrylic acid-containing solution). The operation for accumulation was continued until the concentration of water in the acrylic acid-containing solution 16 became 10 mass % or less. Then, it was confirmed that the concentration of water in the acrylic acid-containing solution 16 discharged from the absorption column 14 became 10 mass % or less and could be obtained in a stable manner. The liquid composition of the acrylic acid-containing solution (the stored acrylic acid-containing solution) stored in the intermediate tank 24 thus far comprised 77.0 mass % of acrylic acid, 15.0 mass % of water and 8.0 mass % of other impurities.

Next, the stored acrylic acid-containing solution in the intermediate tank 24 was supplied from the line 28 to the absorption column 14. The amount of the stored acrylic acid-containing solution supplied then was 20 mass % of a total amount of the absorption liquid, and a usual absorption liquid was used for the rest of the total amount of the absorption liquid.

The liquid composition of the acrylic acid-containing solution 16 thus obtained from the absorption column 14 comprised 89.0 mass % of acrylic acid, 6.0 mass % of water and 5.0 mass % of other impurities. The acrylic acid-containing solution 16 was supplied to the crystallizer 19 for crystallization.

The resultant acrylic acid showed a purity of 99.4 mass %, and the purification yield of acrylic acid was 99.9%.

In this Example 8, although no special operation was carried out except that the acrylic acid-containing solution containing more than 10.0 mass % of water was brought back to the absorption column as the absorption liquid, the purified acrylic acid having high purity could be produced in good yield as described above.

EXAMPLE 9

The acrylic acid-containing gas 12 obtained by the catalytic gas phase oxidation method was subjected to counterflow contact with the absorption liquid 15 in the absorption column 14 to obtain the acrylic acid-containing solution 16. Since the acrylic acid-containing solution 16 had a high concentration of water up to 20.0 mass %, the acrylic acid-containing solution 16 was stored in the intermediate tank 24 (the stored acrylic acid-containing solution). This operation for accumulation was continued until the concentration of water in the acrylic acid-containing solution 16 became 8 mass %. The liquid composition of the acrylic acid-containing solution (the stored acrylic acid-containing solution) thus stored in the intermediate tank 24 comprised 75.0 mass % of acrylic acid, 14.0 mass % of water and 11.0 mass % of other impurities.

Next, the stored acrylic acid-containing solution in the intermediate tank 24 was mixed from the line 35 in the acrylic acid-containing solution 16 (containing 8 mass % or less of water) of the line 38. The mixing mass ratio of the acrylic acid-containing solution to the stored acrylic acid-containing solution was 2:1. The liquid composition of the mixture comprised 81.7 mass % of acrylic acid, 10.0 mass % of water, and 8.3 mass % of other impurities.

The mixture was supplied to the crystallizer 19 for crystallization. The resultant acrylic acid showed a purity of 99.4 mass %, and the purification yield of acrylic acid was 96.0%. In this Example 9, although no special operation was carried out except that the acrylic acid-containing solution containing more than 10.0 mass % of water was temporarily stored, and that the stored acrylic acid-containing solution was mixed in the acrylic acid-containing solution 16 containing 8 mass % or less of water, the purified acrylic acid having high purity could be produced as described above.

In summary of the above results of experiments, separation and purification by crystallization could not be carried out smoothly in Examples 5 and 6, while could be carried out smoothly in the crystallizer 19 to obtain the purified acrylic acid having high purity in Examples 1 to 4 and 7 to 9. With respect to the yield, a high yield was obtained in Examples 1 to 4 and 8, but in Examples 7 and 9 in which an acrylic acid-containing solution having a concentration of water of 10.0 mass % was crystallized, the yield was somewhat inferior to that of Examples 1 to 4 and 8. From the results of the experiments, it is found that by making the concentration of water 10 mass % or less using the above measure [a] to [d] when the acrylic acid-containing solution contains more than 10 mass % of water, the crystallization process can be progressed smoothly, and even more, a high yield can be obtained.

Although the above examples showed methods for producing acrylic acid, the present invention can also be applied to methacrylic acid in a same manner.

According to the present invention, even if the (meth) acrylic acid-containing solution contains more than 10 mass % of water, which is an unsteady state, (meth) acrylic acid can be collected from the (meth)acrylic acid-containing solution without any special operation, and the purified acrylic acid having high purity can be obtained at high yield with less loss in the (meth) acrylic acid production process as a whole. Moreover, the steps are easy and simple, and elevation of cost arising on the occasions such as disposal or the additional water separation operation as described above is not induced. This application is based on Japanese Patent Application No. 2006-254955 filed on Sep. 20, 2006, the contents of which are hereby incorporated by reference.

The invention claimed is:

1. A method for producing (meth)acrylic acid comprising:
    obtaining a (meth)acrylic acid-containing gas from a raw material for producing (meth)acrylic acid by a catalytic gas phase oxidation reaction;
    obtaining a (meth)acrylic acid-containing solution from the (meth)acrylic acid-containing gas;
    adjusting a water content of the (meth)acrylic acid-containing solution to 10 mass % or less; and
    subjecting the (meth)acrylic acid-containing solution containing 10 mass % or less of water to a crystallization process, thereby producing a purified (meth)acrylic acid,
    wherein the adjusting of the water content is carried out by mixing a purified (meth)acrylic acid and/or a (meth) acrylic acid-containing solution containing 10 mass % or less of water into a (meth)acrylic acid-containing solution containing more than 10 mass % of water obtained from the (meth)acrylic acid-containing gas.

2. The method for producing (meth)acrylic acid according to claim 1, wherein the purified (meth)acrylic acid is used as the purified (meth)acrylic acid to be mixed in the (meth) acrylic acid-containing solution containing more than 10 mass % of water.

3. The method for producing (meth)acrylic acid according to claim 1, wherein a part of the (meth)acrylic acid-containing solution containing 10 mass % or less of water obtained in the production process of (meth)acrylic acid is stored in advance and then mixed in the (meth)acrylic acid-containing solution containing more than 10 mass % of water.

4. The method for producing (meth)acrylic acid according to claim 1, further comprising bringing the (meth)acrylic acid-containing gas in contact with an absorption liquid to obtain the (meth)acrylic acid-containing solution, wherein water is used as the absorption liquid.

5. The method for producing (meth)acrylic acid according to claim 2, wherein a part of the (meth)acrylic acid-containing solution containing 10 mass % or less of water obtained in the production process of (meth)acrylic acid is stored in advance and then mixed in the (meth)acrylic acid-containing solution containing more than 10 mass % of water.

6. The method for producing (meth)acrylic acid according to claim 5, further comprising bringing the (meth)acrylic acid-containing gas in contact with an absorption liquid to obtain the (meth)acrylic acid-containing solution, wherein water is used as the absorption liquid.

7. A method for producing (meth)acrylic acid comprising:
obtaining a (meth)acrylic acid-containing gas from a raw material for producing (meth)acrylic acid by a catalytic gas phase oxidation reaction;
bringing the (meth)acrylic acid-containing gas in contact with an absorption liquid to obtain a (meth)acrylic acid-containing solution containing more than 10 mass % of water;
circulating the (meth)acrylic acid-containing solution containing more than 10 mass % of water as the absorption liquid until a (meth)acrylic acid-containing solution to be subjected to a crystallization process contains 10 mass % or less of water; and
subjecting the (meth)acrylic acid-containing solution containing 10 mass % or less of water to the crystallization process, thereby producing a purified (meth)acrylic acid.

8. The method for producing (meth)acrylic acid according to claim 7 comprising bringing the (meth)acrylic acid-containing gas in contact with an absorption liquid to obtain the (meth)acrylic acid-containing solution, wherein water is concomitantly used as the absorption liquid.

9. A method for producing (meth)acrylic acid comprising:
obtaining a (meth)acrylic acid-containing gas from a raw material for producing (meth)acrylic acid by a catalytic gas phase oxidation reaction;
obtaining a (meth)acrylic acid-containing solution from the (meth)acrylic acid-containing gas, while temporarily storing a (meth)acrylic acid-containing solution containing more than 10 mass % of water obtained from the (meth)acrylic acid-containing gas until a (meth)acrylic acid-containing solution containing 10 mass % or less of water can be obtained in a stable manner;
mixing the temporarily stored (meth)acrylic acid-containing solution into the (meth)acrylic acid-containing solution containing 10 mass % or less of water obtained in the stable manner to an extent of maintaining the water content 10 mass % or less; and
subjecting the (meth)acrylic acid-containing solution containing 10 mass % or less of water to a crystallization process, thereby producing a purified (meth)acrylic acid.

10. The method for producing (meth)acrylic acid according to claim 9, further comprising bringing the (meth)acrylic acid-containing gas in contact with an absorption liquid to obtain the (meth)acrylic acid-containing solution, wherein water is used as the absorption liquid.

11. The method for producing (meth)acrylic acid according to claim 1, further comprising
separating a reaction by-product from the (meth)acrylic acid-containing solution obtained from the (meth)acrylic acid-containing gas before adjusting the water content thereof.

12. The method for producing (meth)acrylic acid according to claim 7, further comprising
separating a reaction by-product from the (meth)acrylic acid-containing solution obtained from the (meth)acrylic acid-containing gas before adjusting the water content thereof.

13. The method for producing (meth)acrylic acid according to claim 9, further comprising
separating a reaction by-product from the (meth)acrylic acid-containing solution obtained from the (meth)acrylic acid-containing gas before adjusting the water content thereof.

* * * * *